United States Patent [19]

Sunkara et al.

[11] Patent Number: 5,648,365

[45] Date of Patent: Jul. 15, 1997

[54] DIARYLALKYL PIPERIDINES USEFUL AS MULTI-DRUG RESISTANT TUMOR AGENTS

[75] Inventors: Sai P. Sunkara, San Diego, Calif.; Jules Freedman, Cincinnati, Ohio

[73] Assignee: Merrell Pharmaceuticals Inc., Cincinnati, Ohio

[21] Appl. No.: 481,538

[22] PCT Filed: Dec. 17, 1993

[86] PCT No.: PCT/US93/12300

§ 371 Date: Mar. 11, 1996

§ 102(e) Date: Mar. 11, 1996

[87] PCT Pub. No.: WO94/17040

PCT Pub. Date: Aug. 4, 1994

Related U.S. Application Data

[63] Continuation of Ser. No. 111,027, Aug. 24, 1993, abandoned, which is a continuation of Ser. No. 6,569, Jan. 21, 1993, abandoned.

[51] Int. Cl.[6] .............. C07D 211/16; C07D 401/06; A61K 31/445; A61K 31/40

[52] U.S. Cl. .............. 514/320; 514/323; 514/330

[58] Field of Search ............... 546/196, 201, 546/226; 514/320, 323, 330

[56] References Cited

U.S. PATENT DOCUMENTS

| | | | |
|---|---|---|---|
| 2,898,339 | 8/1959 | Wheeler et al. | 546/194 |
| 3,956,296 | 5/1976 | Duncan et al. | 544/130 |
| 4,035,372 | 7/1977 | Deason et al. | 546/229 |
| 4,851,423 | 7/1989 | Girijavallab-han et al. | 514/399 |
| 4,990,511 | 2/1991 | Nakajima et al. | 514/255 |

FOREIGN PATENT DOCUMENTS

| | | |
|---|---|---|
| 0235463 | 9/1987 | European Pat. Off. |
| 0467435 | 1/1992 | European Pat. Off. |
| 0471612 | 2/1992 | European Pat. Off. |
| 1188403 | 9/1959 | France |
| 9015599 | 12/1990 | WIPO |
| 9110651 | 7/1991 | WIPO |
| 9316044 | 8/1993 | WIPO |

OTHER PUBLICATIONS

Wu, et al, Cancer Research, 52, pp. 3029–3034, Jun. 1, 1992.
Chemical Abstracts, vol. 67, 32621c, 1967.
Kartner et al., Scientific American, 44–51 (1989).
Tsuruo et al., Cancer Research 43, 2905–2910 (1983).
Helson, Cancer Drug Delivery vol. 1, No. 4, 353–361 (1984).
Tsuruo et al., Cancer Research 43, 2267–2272 (1983).
Gottesman et al., TIPS Reviews vol. 9, 54–58 (1988).
Endicott et al., Annual Review Biochem 58, 137–171 (1989).
Ford, et al., Pharmacological Review, Am. Soc. for Pharmacology and Experimental Therapeutics vol. 42, No. 3, 155–199 (1990).
Chemical Abstracts vol. 102:45760p (1985).
Chemical Abstracts vol. 102:2490F 19(9), 671–675 (1983).
Chemical Abstracts 67:3262c Ghiringhelli et al., (1967).

Primary Examiner—Richard L. Raymond
Attorney, Agent, or Firm—Nelsen L. Lentz

[57] ABSTRACT

Diarylalkyl piperidines of formula (1)

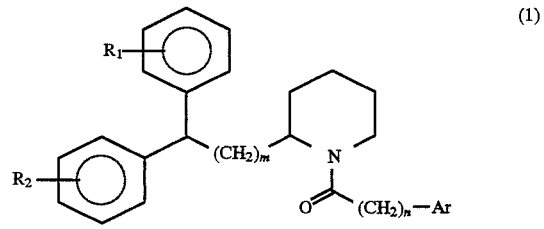

reverse drug resistance in multi-drug resistant tumors. These compounds apparently function by inhibiting a p-glycoprotein pump which becomes activated in late stage tumor development and which is inherently present in tumors from certain origins.

6 Claims, No Drawings

DIARYLALKYL PIPERIDINES USEFUL AS MULTI-DRUG RESISTANT TUMOR AGENTS

The present application is a 371 of PCT/US93/12300 filed Dec. 17, 1993 which is a continuation of application Ser. No. 08/111,027, filed Aug. 24, 1993, now abandoned, which is a continuation of application Ser. No. 08/006,569, filed Jan. 21, 1993, now abandoned.

BACKGROUND OF THE INVENTION

Effective tumor treatment is frequently thwarted by the lack of sensitivity of certain tumors to standard chemotherapeutic agents (intrinsic resistance) or by the ability of certain tumors to develop a lack of chemotherapeutic sensitivity during the course of treatment (acquired or extrinsic resistance). The cause of these phenomena has been linked to the existence of an energy dependent efflux pump which acts to remove the chemotherapeutic agent from the target cell. The pump consists of the P-glycoprotein found as a constituent of cell membrane, and it has been suggested that the normal function of the P-glycoprotein is to remove toxins from within the cell. This theory is supported by the observation that P-glycoprotein is found as a cell membrane constituent in cells of liver, kidney, colon, and jejunum tissues. It has been suggested that P-glycoprotein in the cell membrane of such normal tissues could act to remove toxins or to assist in the transport of nutrients and solutes and to secrete a variety of protein and steroid substances. The natural presence of P-glycoprotein in tumor cells derived from these tissues as well as its presence in tumor cells derived from other tissue types could explain, at least in part, resistance of various tumors to therapy with standard chemotherapeutic agents. The use of agents which inactivate the P-glycoprotein pump could be therapeutic and valuable in the treatment of multi-drug resistant tumors.

SUMMARY OF THE INVENTION

This invention relates to novel diarylalkyl piperidines of Formula 1

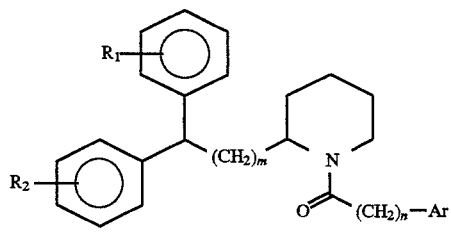

Formula 1 wherein m is an integer selected from the group consisting of 0, 1 or 2, n is an integer selected from the group consisting of 0, 1, 2 or 3, $R_1$ and $R_2$ are each independently selected from the group consisting of hydrogen, halogen, $C_1$–$C_4$ alkyl or $C_1$–$C_4$ alkoxy, and Ar is phenyl, optionally substituted with from 1 to 3 substituents selected from the group consisting of $C_1$–$C_4$ alkyl, $C_1$–$C_4$ alkoxy, $C_1$–$C_4$ alkylthio, halogen, $OCH_2O$, $CF_3$, $OCF_3$, OH, CN, $NO_2$, and $NH_2$; and indolyl, which can be administered with standard chemotherapeutic agents to increase their effectiveness in the treatment of multi-drug resistant tumors.

DETAILED DESCRIPTION OF THE INVENTION

This invention concerns the use of the compounds of Formula 1 as agents effective in reversing drug resistance in multi-drug resistant tumors. The compounds of Formula 1 can be administered together with standard chemotherapeutic agents, can be used in the treatment of tumors which are intrinsically or extrinsically multi-drug resistant, and can be used to reverse resistance in experimental multi-drug resistant tumor cell lines. Multi-drug resistance is defined to be that condition of a tumor cell in which the cell is resistant to a wide variety of unrelated anticancer drugs such as vinca alkaloids, epipodophyllotoxins, dactinomycin, and anthracycline classes as well as colchicine. (Goodman and Gilman, 7th Ed., p. 1278.) This broad based, cross resistance can develop after administration of a single agent of either the vinca alkaloid, epipodophyllotoxins, dactinomycin, and anthracycline classes as well as colchicine and is characterized by resistance to the other members of these drug classes. Examples of antitumor drugs of the vinca alkaloid class include the naturally occurring vincristine and vinblastine as well as the synthetic derivative vindesine. Examples of antitumor drugs of the epipodophyllotoxins class include etoposide and teniposide. An example of an antitumor drug of the anthracycline class is daunorubicin. Examples of antitumor drugs of the dactinomycin class include actinomycin A and actinomycin D.

As used herein, the term "($C_1$–$C_4$)alkoxy" means a straight or branched chain alkoxy group having from one to four carbon atoms such as methoxy, ethoxy, n-propoxy, isopropoxy, n-butoxy, isobutoxy, sec-butoxy, tert-butoxy, and the like.

The compounds of Formula 1 contain one or more asymmetric centers and will therefore exist as enantiomers and diastereomers. In particular the carbon atom of the piperidine ring to which the diphenylalkyl group is attached is an asymmetric center. Moreover, when those phenyls are substituted, not identically, the carbon atom to which these phenyl groups are attached is an asymmetric center. Any reference to the compounds of Formula 1, or any intermediate thereof, should be construed as covering a specific optical isomer, a racemic mixture or a diastereometric mixture. The specific optical isomers can be synthesized or can be separated and recovered by techniques known in the art such as chromatography on chiral stationary phases, resolution via chiral salt formation and subsequent separation by selective crystallization, as is known in the art. Alternatively, a chirally pure starting material may be utilized.

The compounds of the present invention can be prepared as described in Scheme I. All the substituents, unless otherwise indicated, are previously defined. The reagents and starting materials are readily available to one of ordinary skill in the art.

SCHEME I

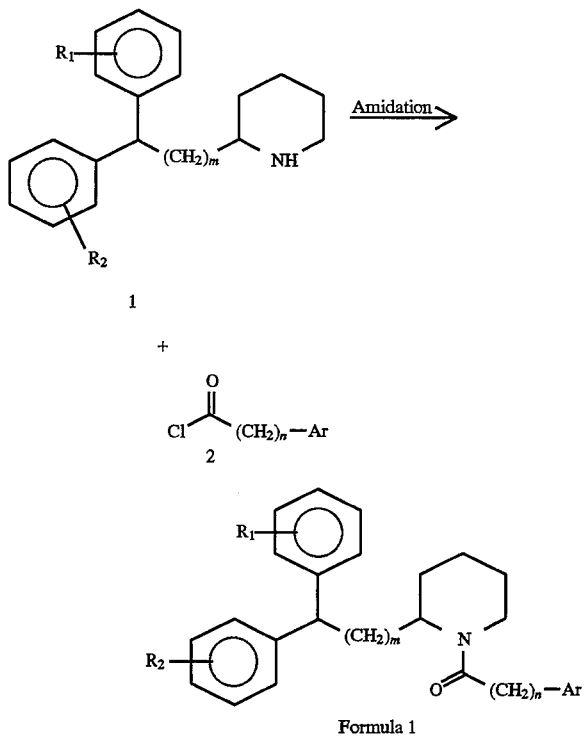

Formula 1

In Scheme I, the appropriately substituted 2-(diphenyl) alkylpiperidine described by structure (1) can be prepared following generally the procedures disclosed in U.S. Pat. No. 3,252,983, May 24, 1966 and Sury, E. et al., *Helv. Chim. Acta.*, 1954, 2133. The 2-(diphenyl)alkylpiperidine can undergo an acylation by treatment with an appropriately substituted acid chloride described by structure (2) to provide the amide described by Formula 1.

For example, 2-(2,2-diphenyl)ethylpiperidine described by structure (2) wherein m=2 and $R_1$ and $R_2$ are hydrogen, is dissolved in a suitable organic solvent, such as methylene chloride with an excess of a suitable trialkylamine, such as triethylamine. The solution is then cooled to approximately 0°–5° C. To this is added dropwise a solution of approximately 1.1 equivalents of an appropriately substituted acid chloride described by structure (2), such as 3,4,5-trimethoxyphenylacetyl chloride in a suitable organic solvent, such as methylene chloride. The reaction is allowed to warm to room temperature and stir for approximately 12 to 24 hours. The desired product described by Formula 1 is then isolated by techniques well known to one skilled in the art. For example, the reaction is rinsed with dilute hydrochloric acid, followed by water, 5% sodium hydroxide and finally saturated sodium chloride. The solvent is removed under vacuum and the residue is crystallized from a suitable organic solvent, such as ethyl acetate to provide the amide described by Formula 1 wherein m=2, $R_1$ and $R_2$ are hydrogen, n=1 and aryl is 3,4,5-tri-methoxyphenyl.

The following examples present typical syntheses as described by Scheme I. These examples are understood to be illustrative only and are not intended to limit the scope of the invention in any way. As used in the following examples, the following terms have the meanings indicated: "g" refers to grams, "mg" refers to milligrams, "mmol" refers to millimoles, "ml" refers to milliliters, and "°C." refers to degrees Celsius.

EXAMPLE 1

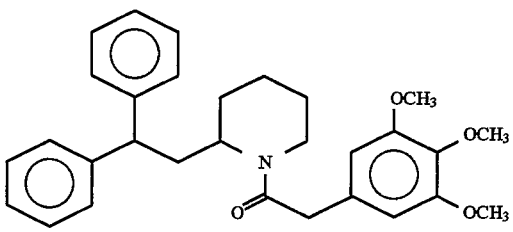

Preparation of 1-[2-(2,2-Diphenyl-Ethyl)-Piperidin-1-yl]-2-(3,4,5-Trimethoxy-Phenyl)-Ethanone Scheme I Cool a solution of triethylamine (1 ml) and 2-(2,2-diphenyl)ethylpiperidine (2.65 g, 0.01 moles) in methylene chloride (50 ml), with an ice bath. To this solution add dropwise a solution of 3,4,5-trimethoxyphenylacetyl chloride (2.69 g, 0.011 moles) in methylene chloride (50 ml). Stir the reaction at room temperature for 12 hours. Rinse the reaction with dilute hydrochloric acid, water, 5% sodium hydroxide and saturated sodium chloride. Concentrate the organic phase under vacuum and crystallize the residue from ethyl acetate to provide the title compound, mp 105°–106° C.

Anal. Calcd for $C_{30}H_{35}NO_4$: C, 76.08; H, 7.45; N, 2.96. Found: C, 75.94; H, 7.46; N, 2.88.

EXAMPLE 2

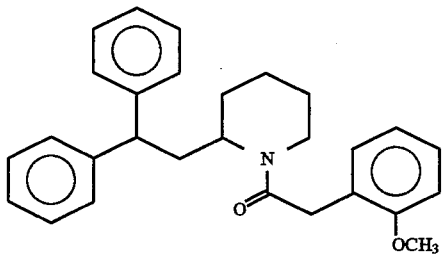

Preparation of 1-[2-(2,2-Diphenyl-Ethyl)-Piperidin-1-yl]-2(2-Methoxy-Phenyl)-Ethanone Scheme I In an analogous manner to example 1, the title compound is prepared as a viscous oil from excess triethylamine, 2-(2,2-diphenyl)ethylpiperidine (1.0 eq) and 2-methoxyphenylacetyl chloride (1.1 eq).

Anal. Calcd for $C_{28}H_{31}NO_4$: C, 81.32; H, 7.56; N, 3.39. Found: C, 80.81; H, 7.58; N, 3.27.

EXAMPLE 3

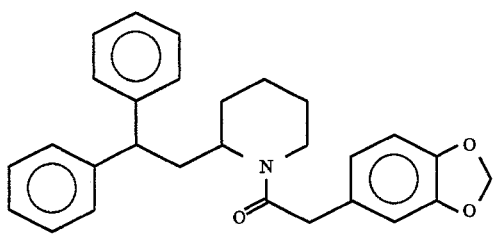

Preparation of 2-Benzo[1,3]Dioxol-5-yl-1-[2-(2,2-Diphenylethyl)-Piperidin-1-yl]-Ethanone Scheme I In an analogous manner to example 1, the title compound, mp 118°–120° C., is prepared from excess triethylamine, 2-(2,2-diphenyl)ethylpiperidine (1.0 eq) and 3,4-(methylenedioxy)phenylacetyl chloride (1.1 eq).

Anal. Calcd for $C_{28}H_{29}NO_3$: C, 78.66; H, 6.84; N, 3.28. Found: C, 78.51; H, 6.71; N, 3.27.

EXAMPLE 4

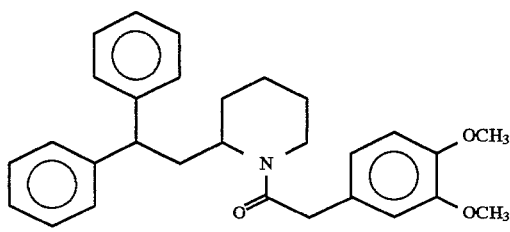

Preparation of 1-[2-(2,2-Diphenyl-Ethyl)-Piperidin-1-yl]-2-(3,4-Dimethoxy-Phenyl)-Ethanone Scheme I In an analogous manner to Example 1, the title compound, mp 113°–114° C., is prepared from excess triethylamine, 2-(2,2-diphenyl)ethylpiperidine (1.0 eq) and 3,4-dimethoxyphenylacetyl chloride (1.1 eq).

Anal. Calcd for $C_{29}H_{33}NO_3$: C, 78.52; H, 7.50; N, 3.16. Found: C, 78.21; H, 7.60; N, 3.01.

EXAMPLE 5

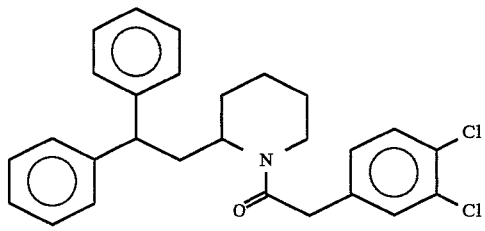

Preparation of 2-(3,4-Dichloro-Phenyl)-1-[2-(2,2-diphenylethyl)-Piperidin-1-yl]-Ethanone Scheme I In an analogous manner to Example 1, the title compound, mp 82°–84° C., is prepared from excess triethylamine, 2-(2,2-diphenyl)ethylpiperidine (1.0 eq) and 3,4-dichlorophenylacetyl chloride (1.1 eq).

Anal. Calcd for $C_{27}H_{27}Cl_2No$: C, 71.68; H, 6.02; N, 3.10 Found: C, 71.60; H, 6.16; N, 3.04.

EXAMPLE 6

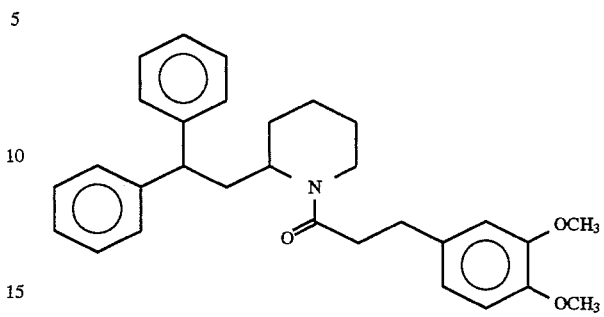

Preparation of 3-(3,4-Dimethoxy-Phenyl)-1-[2-(2,2-Diphenylethyl)-Piperidin-1-yl]-Propan-1-one Scheme I In an analogous manner to Example 1, the title compound, mp 138°–139° C., is prepared from excess triethylamine, 2-(2,2-diphenyl)ethylpiperidine (1.0 eq) and 3-(3,4-dimethoxyphenyl)propionyl chloride (1.1 eq).

Anal. Calcd for $C_{30}H_{35}NO_3$: C, 78.74; H, 7.71; N, 3.06. Found: C, 78.49; H, 7.86; N, 2.87.

EXAMPLE 7

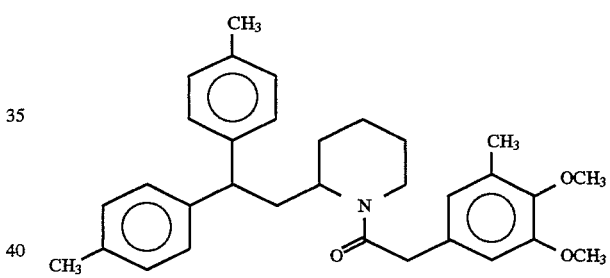

Preparation of 1-[2-(2,2-Di-p-Tolyl-Ethyl)-Piperidin-1-yl]2-(3,4,5-Trimethoxy-Phenyl)-Ethanone Scheme I In an analogous manner to Example 1, the title compound, mp 98°–100° C., is prepared from excess triethylamine, 2-(2,2-(4,4'-ditoluoyl)ethylpiperidine (1.0 eq) and 3,4,5-trimethoxyphenylacetyl chloride (1.1 eq).

Anal. Calcd for $C_{32}H_{39}NO_4$: C, 76.62; H, 7.84; N, 2.79. Found: C, 76.38; H, 7.84; N, 2.71.

EXAMPLE 8

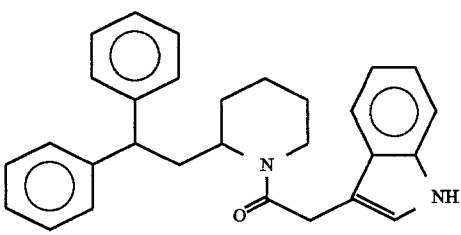

Preparation of 1-[2-(2,2-Diphenyl-Ethyl)-Piperidin-1-yl]-2(1H-Indol-3-yl)-Ethanone Scheme I In an analogous manner to Example 1, the title compound, mp 180°–181° C., is prepared from excess triethylamine, 2-(2,2-diphenyl)ethylpiperidine (1.0 eq) and indole-3-acetyl chloride (1.1 eq).

Anal. Calcd for $C_{29}H_{30}N_2O$: C, 82.43; H, 7.16; N, 6.63. Found: C, 82.56; H, 7.18; N, 6.56.

EXAMPLE 9

Preparation of 1-[2-(Diphenylmethyl)-Piperidin-1-yl]-2(3,4,5-Trimethoxy-Phenyl)-Ethanone Scheme I In an analogous manner to Example 1, the title compound, mp 122°–124° C., is prepared from excess triethylamine, 2-diphenylmethylpiperidine (1.0 eq) and 3,4,5-trimethoxyphenylacetyl chloride (1.1 eq).

Anal. Calcd for $C_{29}H_{33}NO_4$: C, 75.79; H, 7.24; N, 3.05. Found: C, 75.52; H, 7.33; N, 2.98.

DETERMINATION OF MDR ACTIVITY

A colorimetric assay is employed to determine the synergy between test compounds of the invention and vinblastine or adriamycin against the growth of MDR tumor cells. The assay is based on the ability of live tumor cells to reduce a tetrazoline compound, MTT (3-(4,5-dimethyl)imazol-2-yl)-2,5-diphenyl tetrazolium bromide, to a blue formazan product. Both the test compound and cytotoxic drug (vinblastine or adriamycin) were added to the cells growing in wells of a 96-well plate at different combinations of concentration. The cells were allowed to grow for 72 hr and, at the end of incubation, stained with MTT for 3 hr. The blue formazan product which developed, was dissolved with DMSO and the color intensity was recorded in a spectrophotometer. Based on the data, an isobologram analysis was performed. MDR activity ($ED_{50}$: μM) represents the concentration of the compound required to lower the $IC_{50}$ value of vinblastine by 50% when both the compounds were added to the medium together. Cellular toxicity ($IC_{50}$: μM) represents concentration of the compound that inhibit cell growth by 50%. Activity index is the ratio of toxicity and MDR activity.

TABLE 1

MDR ACTIVITY OF DIARYLALKYL PIPERIDINES

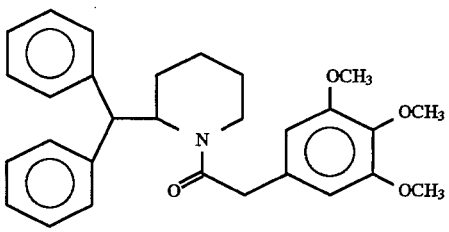

| Ar | m | n | MDR Activity $ED_{50}$ μM | Toxicity (IC50 μM) | Activity Index |
|---|---|---|---|---|---|
| ∅ 3,4,5-$(OCH_3)_3$ | 1 | 1 | 0.31 | 33.8 | 109.0 |
| ∅ 3,4-$(OCH_3)_2$ | 1 | 2 | 0.46 | 21.6 | 47.0 |
| ∅ 3,4,5-$OCH_3$ | 0 | 1 | 0.70 | 30.3 | 43.5 |
| ∅ 3,4-$(OCH_2O)$ | 1 | 1 | 1.20 | 39.0 | 32.5 |
| ∅ 2-$OCH_3$ | 1 | 1 | 1.16 | 37.5 | 32.0 |

The term "patient" used herein is taken to mean mammals such as primates, including humans, and animals such as sheep, horses, cattle, pigs, dogs, cats, rats and mice.

The amount of the diarylalkyl piperidine derivative of Formula 1 to be administered can vary widely according to the particular dosage unit employed, the period of treatment, the age and sex of the patient treated, the nature and extent of the multi-drug resistance in the tumor to be treated, and the particular diarylalkyl piperidine derivative selected. The diarylalkyl piperidine derivative is used in conjunction with other chemotherapeutic agents known to be useful in the treatment of tumors. The amount of a diarylalkyl piperidine derivative of Formula 1 effective to reverse multi-drug resistance will generally range from about 15 mg/kg to 500 mg/kg. A unit dosage may contain from 25 to 500 mg of the diarylalkyl piperidine derivative, and can be taken one or more times per day. The diarylalkyl piperidine derivative can be administered with a pharmaceutical carrier using conventional dosage unit forms either orally or parenterally.

Treatment of tumors by the method of this invention requires that an antitumor effective amount of a chemotherapeutic agent be administered together with a compound of Formula 1. Tumors which can be treated by the method of this invention include both benign and malignant tumors or neoplasms, and include melanomas, lymphomas, leukemias, and sarcomas. Illustrative examples of tumors are cutaneous tumors, such as malignant melanomas and mycosis fungoids; hematologic tumors such as ieukemias, for example, acute lymphoblastic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder or testis; soft tissue sarcomas, osseous or non-osseous sarcomas, breast tumors; tumors of the pituitary, thyroid and adrenal cortex; gastrointestinal tumors, such as those of the esophagus, stomach, intestine and colon; pancreatic and hepatic tumors; laryngeal papillomestasas and lung tumors. Of course those tumors which typically are or become multi-drug resistant are most beneficially treated with the compounds and methods of this invention. Such tumors include colon tumors, lung tumors, stomach tumors, and liver tumors.

The chemotherapeutic agents used together with the diarylalkyl piperidines of Formula 1 are those cytotoxic agents commonly used in the treatment of tumors. Illustrative examples of chemotherapeutic agents are: cyclophosphamide, methotrexate, prednisone, 6-mercaptopurine, procarbazine, daunorubicin, vincristine, vinblastine, chlorambucil, cytosine arabinoside, 6-thioguanine, thio TEPA, 5-fluorouracil, 5-fluoro-2deoxyudirinde, 5-azacytidine, nitrogen mustard, 1,3-bis (2chloroethyl)-1-nitrosourea (BCNU), (1-(2-chloroethyl)-3cyclohexyl-1-nitrosourea) (CCNU), busulfan, adriamycin, bleomycin, vindesine, cycloleucine or methylglyoxal bis (guanylhydrazone) (i.e., MGBG). The effective amount of chemotherapeutic agent used in the method of this invention varies widely and depends on factors such as the patient, the tumor tissue type and its size, and the particular chemotherapeutic agent selected. The amount is any effective amount and can be readily determined by those skilled in the art. In general, less chemotherapeutic agent will be required when administered with the diarylalkyl piperidines of Formula 1, primarily because the problem of drug resistance need not addressed by the addition of larger quantities of chemotherapeutic agent. Of course mixtures of chemotherapeutic agents may be employed and surgical excision and radiation therapy may be useful adjuvants as in any tumor therapy. While the compound of Formula 1 and the chemotherapeutic agent are said to be administered together, this does not necessarily mean that the compounds are formulated into the same dosage form or are administered concurrently. Rather, the expression "together" means that a compound of Formula 1 and the chemotherapeutic agent(s) are administered in a combined dosage form or separately during the course of therapy.

The preferred route of administration is oral administration. For oral administration the derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the breakup and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the esthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The diarylalkyl piperidine derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethyleneglycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-β-aminopropionates, and 2-alkylimidazoline quaternary ammonium salts, as well as mixtures. The parenteral compositions of this invention will typically contain from about 0.5 to about 25% by weight of the oxazolone derivative of Formula 1 in solution. Preservatives and buffers may also be used advantageously.

In order to minimize or eliminate irritation at the site of injection, the compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients.

Preferably topical administration will be accomplished using a patch either of the reservoir and porous membrane type or of a solid matrix variety. Some suitable transdermal devices are described in U.S. Pat. Nos. 3,742,951, 3,797, 494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is nonporous. The pharmaceutically effective compound dissolves in and diffuses through the matrix itself. Release by microporous flow occurs when the pharmaceutically effective compound is transported through a liquid phase in the pores of the matrix.

What is claimed is:

1. A method of reversing drug resistance in multi-drug resistant tumors by administering to a patient in need of such treatment an effective amount of a compound of the formula

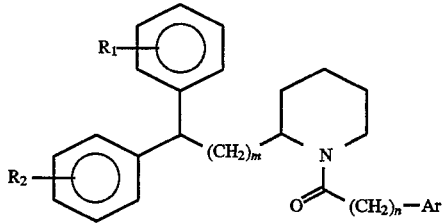

wherein m is an integer selected from the group consisting of 0, 1 or 2, n is an integer selected from the group consisting of 0, 1, 2 or 3, $R_1$ and $R_2$ are each independently selected from the group consisting of hydrogen, halogen, $C_1$–$C_4$ alkyl or $C_1$–$C_4$ alkoxy, and Ar is phenyl optionally substituted with from 1 to 3 substituents selected from the group consisting of $C_1$–$C_4$ alkyl, $C_1$–$C_4$ alkoxy, $C_1$–$C_4$ alkylthio, halogen, $OCH_2O$, $CF_3$, $OCF_3$, OH, CN, $NO_2$, and $NH_2$; or indolyl.

2. A method according to claim 1 wherein m and n are 1, Ar is 3,4,5-trimethoxphenyl, and $R_1$ and $R_2$ are hydrogen.

3. A method according to claim 1 wherein m and n are 1, Ar is 3,4-methylenedioxyphenyl, and $R_1$ and $R_2$ are hydrogen.

4. A method according to claim 1 wherein m is 1, n is 2, Ar is 3,4-dimethoxyphenyl, and $R_1$ and $R_2$ are hydrogen.

5. A method according to claim 1 wherein m is 0, n is 1, Ar id 3,4,5-trimethoxyphenyl, and $R_1$ and $R_2$ are hydrogen.

6. A method according to claim 1 wherein m and n are 1, Ar is 2-methoxyphenyl, and $R_1$ and $R_2$ are hydrogen.

* * * * *